(12) United States Patent
Hills et al.

(10) Patent No.: US 9,684,418 B1
(45) Date of Patent: Jun. 20, 2017

(54) SELF AND MUTUAL CAPACITANCE MEASUREMENT IN A TOUCH SCREEN

(71) Applicant: Parade Technologies, Ltd., Santa Clara, CA (US)

(72) Inventors: Michael Patrick Hills, Lynnwood, WA (US); Volodymyr Burkovskyy, Lviv (UA); Oleksandr Karpin, Lviv (UA); Seok-Pyong Park, Seoul (KR); Patrick Prendergast, Clinton, WA (US)

(73) Assignee: PARADE TECHNOLOGIES, LTD., Santa Clara, CA (US)

( * ) Notice: Subject to any disclaimer, the term of this patent is extended or adjusted under 35 U.S.C. 154(b) by 118 days.

(21) Appl. No.: 14/325,582

(22) Filed: Jul. 8, 2014

Related U.S. Application Data

(63) Continuation of application No. 13/075,762, filed on Mar. 30, 2011, now Pat. No. 8,773,146.

(60) Provisional application No. 61/325,124, filed on Apr. 16, 2010.

(51) Int. Cl.
| | |
|---|---|
| *G01R 27/26* | (2006.01) |
| *G06F 3/041* | (2006.01) |
| *G06F 3/045* | (2006.01) |
| *G06F 3/044* | (2006.01) |
| *G01N 27/22* | (2006.01) |

(52) U.S. Cl.
CPC .............. *G06F 3/044* (2013.01); *G06F 3/041* (2013.01); *G06F 3/0416* (2013.01); *G01N 27/22* (2013.01)

(58) Field of Classification Search
CPC ......... G06F 3/044; G06F 3/041; G06F 3/0416
USPC .................. 324/662, 663, 658; 345/173, 174
See application file for complete search history.

(56) References Cited

U.S. PATENT DOCUMENTS

| | | |
|---|---|---|
| 6,283,504 B1 | 9/2001 | Stanley et al. |
| 6,504,530 B1 | 1/2003 | Wilson et al. |
| 8,054,296 B2 | 11/2011 | Land et al. |
| 2005/0001633 A1 | 1/2005 | Okushima et al. |
| 2008/0136792 A1 | 6/2008 | Peng et al. |
| 2008/0158146 A1 | 7/2008 | Westerman |
| 2008/0158174 A1 | 7/2008 | Land et al. |
| 2008/0158182 A1 | 7/2008 | Westerman |
| 2009/0009485 A1 | 1/2009 | Bytheway |
| 2009/0073140 A1 | 3/2009 | Fujita et al. |
| 2009/0174676 A1 | 7/2009 | Westerman |
| 2009/0322351 A1 | 12/2009 | Mcleod |
| 2010/0007631 A1 | 1/2010 | Chang |
| 2010/0060608 A1 | 3/2010 | Yousefpor |

(Continued)

OTHER PUBLICATIONS

U.S. Appl. No. 13/075,762: "Waterproof Scanning of a Capacitive Sense Array" Michael Patrick Hills et al., filed Mar. 30, 2011; 41 pages.

(Continued)

*Primary Examiner* — Amy He
(74) *Attorney, Agent, or Firm* — Morgan, Lewis & Bockius LLP

(57) ABSTRACT

A water-resistant capacitance sensing apparatus comprising a plurality of capacitive sense elements and a capacitance sensing circuit configured to measure both the mutual capacitance and self-capacitance on the plurality of capacitive sense elements.

A method for water-resistant capacitance sensing, the method comprising performing a self-capacitance scan and a mutual capacitance scan, and detecting, by a processing device, a presence of an object with the plurality of sense elements. The method further determines whether the detected presence of the object is legitimate.

20 Claims, 9 Drawing Sheets

(56) References Cited

U.S. PATENT DOCUMENTS

2010/0328262 A1 12/2010 Huang et al.
2012/0050214 A1 3/2012 Kremin et al.

OTHER PUBLICATIONS

USPTO Advisory Action for U.S. Appl. No. 13/075,762 dated Jan. 3, 2014; 2 pages.
USPTO Final Rejection for U.S. Appl. No. 13/075,762 dated Oct. 18, 2013; 17 pages.
USPTO Non Final Rejection for U.S. Appl. No. 13/075,762 dated Jun. 20, 2013; 12 pages.
USPTO Notice of Allowance for U.S. Appl. No. 13/075,762 dated May 20, 2014; 8 pages.

SELF AND MUTUAL CAPACITANCE MEASUREMENT IN A TOUCH SCREEN

RELATED APPLICATION

This application is a continuation of U.S. patent application Ser. No. 13/075,762, filed Mar. 30, 2011, now U.S. Pat. No. 8,773,146, issued Jul. 8, 2014, which claims priority to U.S. Provisional Patent Application No. 61/325,124 filed Apr. 16, 2010, all of which are incorporated by reference herein in their entirety.

TECHNICAL FIELD

This disclosure relates to the field of user interface devices and, in particular, to capacitive sense devices.

BACKGROUND

Capacitive touch sense elements may be used to replace mechanical buttons, knobs and other similar mechanical user interface controls. The use of a capacitive sense element allows for the elimination of complicated mechanical switches and buttons, providing reliable operation under harsh conditions. Capacitive touch sense elements can be arranged in the form of a sense array for a touch-sense surface. When a conductive object, such as a finger, comes in contact or close proximity with the touch-sense surface, the capacitance of one or more capacitive touch sense elements changes. The capacitance changes of the capacitive touch sense elements can be measured by an electrical circuit. The electrical circuit converts the measured capacitances of the capacitive touch sense elements into digital values.

In practice, contemporary capacitive touch sense elements find use in a wide variety of modern customer applications including laptops, cell phones, and automotive applications, which may be exposed to widely varying environmental conditions. For example, moisture, high humidity, or sharp changes in the ambient temperature may adversely affect the electrical characteristics of the capacitive touch sense elements, causing the tracking algorithms to report false touches or ignore real touches. This results in inaccurate and unreliable position tracking in many real-world applications.

BRIEF DESCRIPTION OF THE DRAWINGS

The present invention is illustrated by way of example, and not of limitation, in the figures of the accompanying drawings in which.

DETAILED DESCRIPTION

In the following description, for purposes of explanation, numerous specific details are set forth in order to provide a thorough understanding of the present invention. It will be evident, however, to one skilled in the art that the present invention may be practiced without these specific details. In other instances, well-known circuits, structures, and techniques are not shown in detail, but rather in a block diagram in order to avoid unnecessarily obscuring an understanding of this description.

Reference in the description to "one embodiment" or "an embodiment" means that a particular feature, structure, or characteristic described in connection with the embodiment is included in at least one embodiment of the invention. The phrase "in one embodiment" located in various places in this description does not necessarily refer to the same embodiment.

Figure 1:
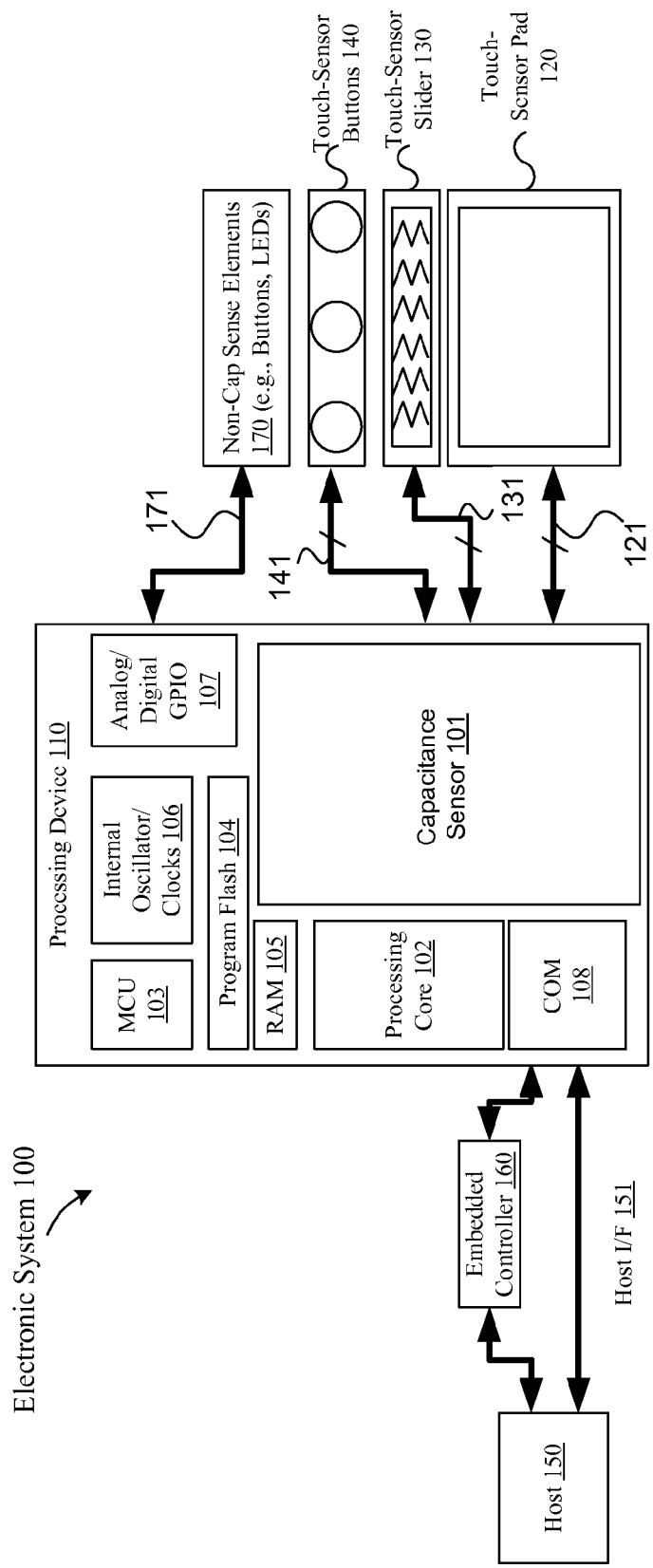
FIG. 1 is a block diagram illustrating one embodiment of an electronic system having a processing device for detecting a presence of a conductive object according to an embodiment of the present invention.

FIG. 1 is a block diagram illustrating one embodiment of an electronic system 100 having a processing device for detecting a presence of a conductive object according to an embodiment of the present invention. Electronic system 100 includes processing device 110, touch-sense pad 120, touch-sense slider 130, touch-sense buttons 140, host processor ("host") 150, embedded controller 160, and non-capacitive sense elements 170. The processing device 110 may include analog and/or digital general purpose input/output ("GPIO") ports 107. GPIO ports 107 may be programmable. GPIO ports 107 may be coupled to a Programmable Interconnect and Logic ("PIL"), which acts as an interconnect between GPIO ports 107 and a digital block array of the processing device 110 (not shown). The digital block array may be configured to implement a variety of digital logic circuits (e.g., DACs, digital filters, or digital control systems) using, in one embodiment, configurable user modules ("UMs"). The digital block array may be coupled to a system bus. Processing device 110 may also include memory, such as random access memory ("RAM") 105 and program flash 104. RAM 105 may be static RAM ("SRAM"), and program flash 104 may be a non-volatile storage, which may be used to store firmware (e.g., control algorithms executable by processing core 102 to implement operations described herein). Processing device 110 may also include a memory controller unit ("MCU") 103 coupled to memory and the processing core 102.

The processing device 110 may also include an analog block array (not shown). The analog block array is also coupled to the system bus. Analog block array also may be configured to implement a variety of analog circuits (e.g., ADCs or analog filters) using, in one embodiment, configurable UMs. The analog block array may also be coupled to the GPIO ports 107.

As illustrated, capacitance sensor circuit ("capacitance sensor") 101 may be integrated into processing device 110. Capacitance sensor 101 may include analog I/O for coupling to an external component, such as touch-sense pad 120, touch-sense slider 130, touch-sense buttons 140, and/or other devices. Capacitance sensor 101 and processing device 110 are described in more detail below.

The embodiments described herein are not limited to touch-sense pads for notebook implementations, but can be used in other capacitive sensing implementations, for example, the sensing device may be a touch screen, a touch-sense slider 130, or touch-sense buttons 140 (e.g., capacitance sense buttons). In one embodiment, these sensing devices include one or more capacitive sense elements. The operations described herein are not limited to notebook pointer operations, but can include other operations, such as lighting control (dimmer), volume control, graphic equalizer control, speed control, or other control operations requiring gradual or discrete adjustments. It should also be noted that these embodiments of capacitive sense implementations may be used in conjunction with non-capacitive sense elements, including but not limited to pick buttons, sliders (ex. display brightness and contrast), scroll-wheels, multimedia control (ex. volume, track advance, etc) handwriting recognition and numeric keypad operation.

In one embodiment, the electronic system 100 includes a touch-sense pad 120 coupled to the processing device 110 via bus 121. Touch-sense pad 120 may include a multi-dimension sense array. The multi-dimension sense array includes multiple sense elements, organized as rows and columns. In another embodiment, the electronic system 100 includes a touch-sense slider 130 coupled to the processing device 110 via bus 131. Touch-sense slider 130 may include a single-dimension sense array. The single-dimension sense array includes multiple sense elements, organized as rows, or alternatively, as columns. In another embodiment, the electronic system 100 includes touch-sense buttons 140 coupled to the processing device 110 via bus 141. Touch-sense buttons 140 may include a single-dimension or multi-dimension sense array. The single- or multi-dimension sense array may include multiple sense elements. For a touch-sense button, the sense elements may be coupled together to detect a presence of a conductive object over the entire surface of the sensing device. Alternatively, the touch-sense buttons 140 may have a single sense element to detect the presence of the conductive object. In one embodiment, touch-sense buttons 140 includes a capacitive sense element. Capacitive sense elements may be used as non-contact sense elements. These sense elements, when protected by an insulating layer, offer resistance to severe environments.

The electronic system 100 may include any combination of one or more of the touch-sense pad 120, touch-sense slider 130, and/or touch-sense button 140. In another embodiment, the electronic system 100 may also include non-capacitance sense elements 170 coupled to the processing device 110 via bus 171. The non-capacitance sense elements 170 may include buttons, light emitting diodes ("LEDs"), and other user interface devices, such as a mouse, a keyboard, or other functional keys that do not require capacitive sensing. In one embodiment, buses 171, 141, 131, and 121 are embodied in a single bus. Alternatively, these buses may be configured into any combination of one or more separate buses.

Processing device 110 may include internal oscillator/clocks 106 and communication block ("COM") 108. The oscillator/clocks block 106 provides clock signals to one or more of the components of processing device 110. Communication block 108 may be used to communicate with an external component, such as a host processor 150, via host interface ("I/F") line 151. Alternatively, processing device 110 may also be coupled to embedded controller 160 to communicate with the external components, such as host 150. In one embodiment, the processing device 110 is configured to communicate with the embedded controller 160 or the host 150 to send and/or receive data.

Processing device 110 may reside on a common carrier substrate such as, for example, an integrated circuit ("IC") die substrate, a multi-chip module substrate, or the like. Alternatively, the components of processing device 110 may be one or more separate integrated circuits and/or discrete components. In one exemplary embodiment, processing device 110 is a Programmable System on a Chip ("PSoC™") processing device, manufactured by Cypress Semiconductor Corporation, San Jose, Calif. Alternatively, processing device 110 may be one or more other processing devices known by those of ordinary skill in the art, such as a microprocessor or central processing unit, a controller, special-purpose processor, digital signal processor ("DSP"), an application specific integrated circuit ("ASIC"), a field programmable gate array ("FPGA"), or the like.

It should also be noted that the embodiments described herein are not limited to having a configuration of a processing device coupled to a host, but may include a system that measures the capacitance on the sensing device and sends the raw data to a host computer where it is analyzed by an application. In effect the processing that is done by processing device 110 may also be done in the host.

Capacitance sensor 101 may be integrated into the IC of the processing device 110, or alternatively, in a separate IC. Alternatively, descriptions of capacitance sensor 101 may be generated and compiled for incorporation into other integrated circuits. For example, behavioral level code describing capacitance sensor 101, or portions thereof, may be generated using a hardware descriptive language, such as VHDL or Verilog, and stored to a machine-accessible medium (e.g., CD-ROM, hard disk, floppy disk, etc.). Furthermore, the behavioral level code can be compiled into register transfer level ("RTL") code, a netlist, or even a circuit layout and stored to a machine-accessible medium. The behavioral level code, the RTL code, the netlist, and the circuit layout all represent various levels of abstraction to describe capacitance sensor 101.

It should be noted that the components of electronic system 100 may include all the components described above. Alternatively, electronic system 100 may include only some of the components described above.

In one embodiment, electronic system 100 is used in a notebook computer. Alternatively, the electronic device may be used in other applications, such as a mobile handset, a personal data assistant ("PDA"), a keyboard, a television, a remote control, a monitor, a handheld multi-media device, a handheld video player, a handheld gaming device, or a control panel.

Figure 2:
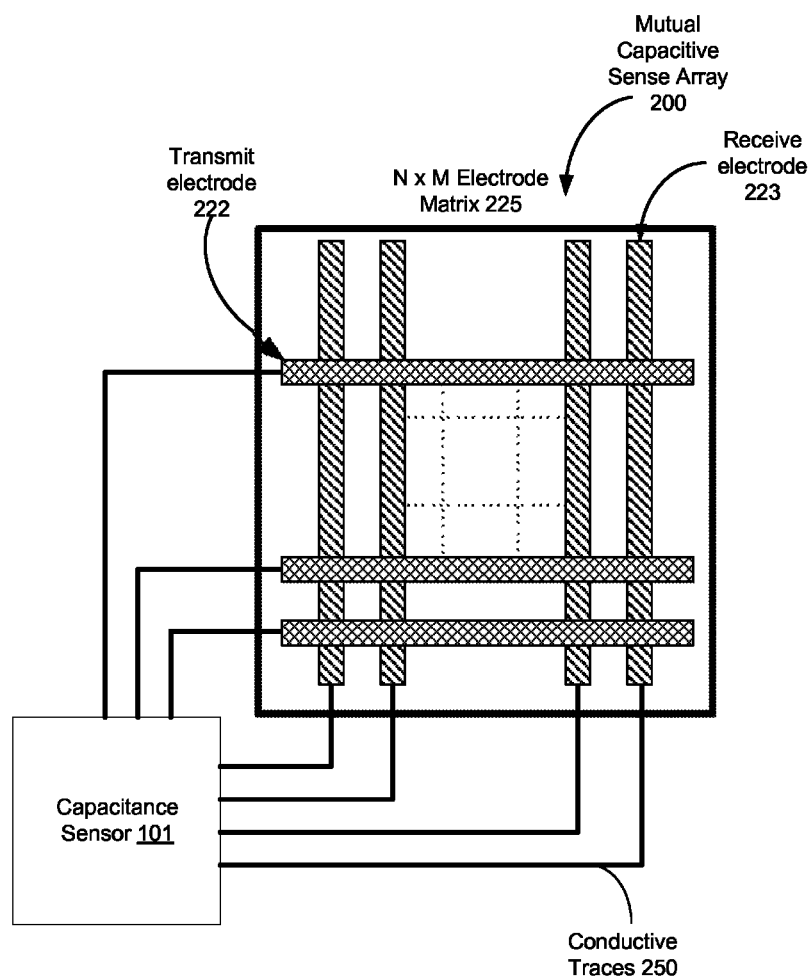
FIG. 2 is a block diagram illustrating one embodiment of a mutual capacitive touchpad sense array and a capacitance sensor that converts measured capacitances to touchpad coordinates.

FIG. 2 is a block diagram illustrating one embodiment of a mutual capacitive touchpad sense array ("sense array") 200 comprising an N×M electrode matrix 225 and a capacitance sensor 101 that converts measured capacitances to touchpad coordinates. The mutual capacitance sense array 200 may be, for example, the touch-sense pad 120 of FIG. 1. The N×M electrode matrix 225 includes N×M electrodes (N receive electrodes and M transmit electrodes), which further includes transmit ("TX") electrode 222 and receive ("RX") electrode 223. Each of the electrodes in N×M electrode matrix 225 is connected with capacitance sensor 101 by conductive traces 250. In one embodiment, capacitance sensor 101 operates using a charge accumulation circuit, capacitive bridge divider, current versus voltage shift measurement, or other method known by those skilled in the art.

The transmit and receive electrodes in the N×M electrode matrix 225 are arranged so that each of the transmit electrodes intersects each of the receive electrodes. Thus, each transmit electrode is capacitively coupled with each of the receive electrodes. For example, transmit electrode 222 is capacitively coupled with receive electrode 223 at the point where transmit electrode 222 and receive electrode 223 intersect.

Because of the capacitive coupling between the transmit and receive electrodes, a TX signal (not shown) applied to each transmit electrode induces a current at each of the receive electrodes. For instance, when a TX signal is applied to transmit electrode 222, the TX signal induces an RX signal (not shown) on the receive electrode 223 in N×M electrode matrix 225. The RX signal on each of the receive electrodes can then be measured in sequence by using a multiplexor to connect each of the N receive electrodes to a demodulation circuit in sequence. The capacitance associated with each intersection between a TX electrode and an RX electrode can be sensed by selecting every available combination of TX electrode and RX electrode.

When an object, such as a finger, approaches the N×M electrode matrix 225, the object causes a decrease in capacitance affecting only some of the electrodes. For example, if a finger is placed near the intersection of transmit electrode 222 and receive electrode 223, the presence of the finger will decrease the capacitance between the transmit electrode 222 and receive electrode 223. Thus, the location of the finger on the touchpad can be determined by identifying both the receive electrode having a decreased capacitance and the transmit electrode to which the TX signal was applied at the time the decreased capacitance was measured on the receive electrode. Thus, by sequentially determining the capacitances associated with each intersection of electrodes in the N×M electrode matrix 225 the locations of one or more inputs can be determined. The conversion of the induced current waveform to touch coordinates indicating a position of an input on a touch sense pad is known to those skilled in the art.

Although the transmit and receive electrodes 222, 223, appear as bars or elongated rectangles in FIG. 2, alternative embodiments may use various tessellated shapes such as rhomboids, chevrons, and other useable shapes known by those skilled in the art. In one embodiment, the transmit and receive electrodes 222, 223, are diamonds, similar to the self-capacitive sense array 400 of FIG. 4 below.

Figure 3:
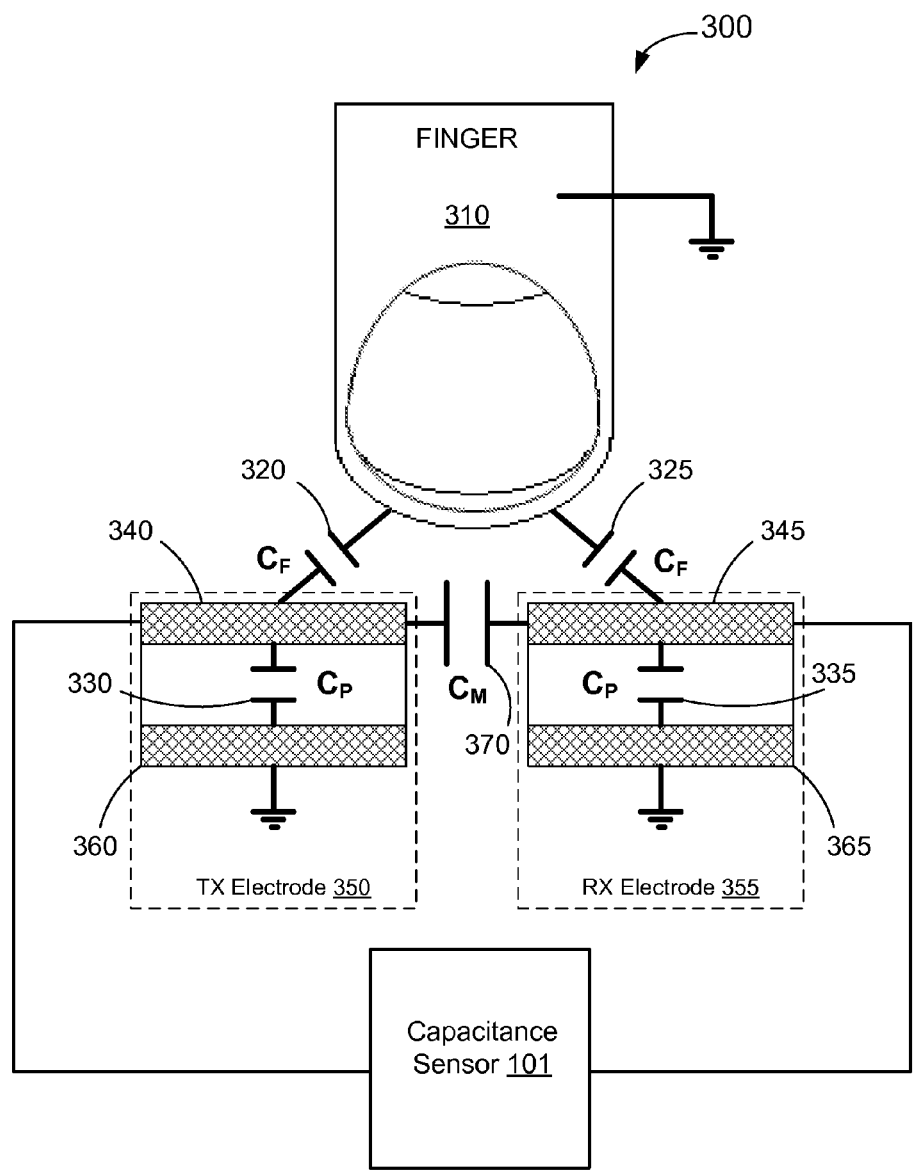
FIG. 3 illustrates the electrical characteristics of a pair of transmit-receive capacitive sense elements according to an embodiment of the present invention.

FIG. 3 illustrates the electrical characteristics of a pair TX-RX capacitive sense elements 300 ("TX-RX 300") according to an embodiment of the present invention. The TX-RX 300 includes a finger 310, a TX electrode 350, an RX electrode 355, and a capacitance sensor 101. The TX electrode 350 includes an upper conductive plate 340 ("UCP 340") and a lower conductive plate 360 ("LCP 360"). The RX electrode 355 includes an upper conductive plate 345 ("UCP 345") and a lower conductive plate 365 ("LCP 365").

The capacitance sensor 101 is electrically connected to the upper conductive plates 340 and 345 of TX electrode 350 and RX electrode 355, respectively. The upper conductive plates 340 and 345 are separated from the lower conductive plates 360 and 365, respectively, by air, dielectric, or any non-conductive material known to those skilled in the art. Similarly, the upper conductive plates 340 and 345 are separated from one another by air or dielectric material. The finger 310 and lower conductive plates 360 and 365 are electrically grounded.

Each of the transmit and receive electrodes 350 and 355, respectively, has a parasitic capacitance $C_P$ and a mutual capacitance $C_M$. The parasitic capacitance of a sense element (TX/RX electrode) is the capacitance between the sense element and ground. In the TX electrode 350, the parasitic capacitance is the capacitance between the UCP 340 and the LCP 360 as depicted by $C_P$ 330. In the RX electrode 355, the parasitic capacitance is the capacitance between the UCP 345 and the LCP 365 as depicted by $C_P$ 335. The mutual capacitance of a sense element is the capacitance between the sense element and other sense elements. Here, the mutual capacitance is the capacitance between TX electrode 350 and RX electrode 355, denoted as $C_M$ 370.

The proximity of an object, such as a finger 310, near the TX electrode 350 and RX electrode 355 may change the capacitance between the electrodes as well as the capacitance between the electrodes and ground. The capacitance between the finger 310 and the electrodes is shown in FIG. 3 as $C_F$ 320 and $C_F$ 325. $C_F$ 320 is the capacitance between the UCP 340 and the finger 310. $C_F$ 325 is the capacitance between the UCP 345 and the finger 310. The magnitude of the change in capacitance induced by the finger 310 can be detected and converted to a voltage level or a digital code that can be processed by a computer or other circuit as described above. In one exemplary embodiment, Cf ranges between 10-30 picofarads (pF). Alternatively, other ranges may occur.

The measured capacitance of the sense elements as seen from capacitance sensor 101 includes the parasitic and mutual capacitances $C_P$ and $C_M$ in addition to $C_F$. The baseline capacitance may be described as the capacitance of the sense element when no input (i.e., a finger touch) is present, or $C_P$ and $C_M$. The capacitance sensor 101 and supporting circuitry are configured to resolve a difference between the baseline capacitance and the capacitance including $C_F$ in order to accurately detect a legitimate presence of a conductive object. This is further discussed in FIG. 2 and is generally known to those skilled in the art.

Figure 4:
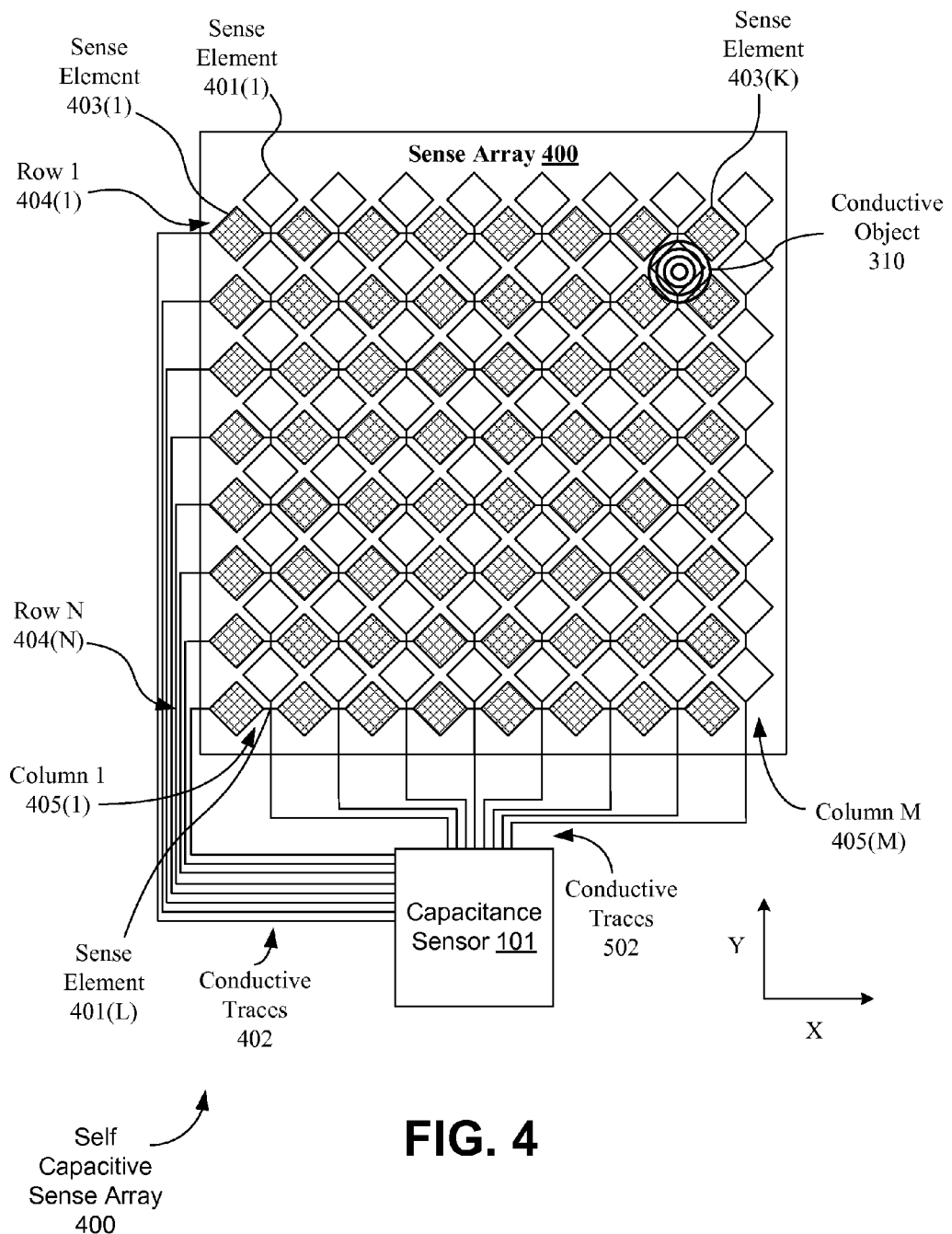
FIG. 4 illustrates a top-side view of one embodiment of a sense array of sense elements for detecting a presence of a conductive object on the self-capacitive sense array of a touch-sense pad.

FIG. 4 illustrates a top-side view of one embodiment of a sense array of sense elements for detecting a presence of a conductive object 303 on the self-capacitive sense array 400 of a touch-sense pad. Sense array 400 includes rows 404 (1)-404(N) and columns 405(1)-405(M), where N is a positive integer value representative of the number of rows and M is a positive integer value representative of the number of columns. Each row includes sense elements 403(1)-403(K), where K is a positive integer value representative of the number of sense elements in the row. Each column includes sense elements 401(1)-401(L), where L is a positive integer value representative of the number of sense elements in the column. Accordingly, the sense array is an N×M sense matrix. The N×M sense matrix, in conjunction with the capacitance sensor 101 through conductive traces 402, is configured to detect a position of a presence of the finger (i.e, conductive object) 310 in the x-, and y-directions. In reference to FIG. 3, the capacitance sensor 101 is connected between UCP 345 and LCP 365 to measure the self-capacitance of RX electrode 355, according to one embodiment. In another embodiment, the sense array is a 1×M or N×1 sense matrix that can be configured to operate as a touch-sense slider.

Alternating sense elements in FIG. 4 correspond to x- and y-axis elements. The y-axis sense elements 403(1)-403(K) for each row 404(1)-404(N) are illustrated as black diamonds. The x-axis sense elements 401(1)-401(L) for each column 405(1)-405(M) are illustrated as white diamonds. It should be noted that other shapes, such as hexagons, chevrons, or other tessellatable shapes known by those skilled in the art may be used for the sense elements.

In one embodiment, the sense array 400 is arranged in conjunction with a liquid-crystal display (LCD) (not shown), where the boundaries and dimensions of the LCD display are similar and align with the sense array 400. In another embodiment, the mutual capacitive touchpad sense array 200 may also be arranged in conjunction with a display. Other types of displays may be used instead of an LCD display. For example, other applicable display technologies include light emitting diodes ("LED"), organic light emitting diodes ("OLED"), nanocrystal displays, carbon nanotube displays, plasma displays, or other flat panel technologies known by those skilled in the art.

Figure 5A:
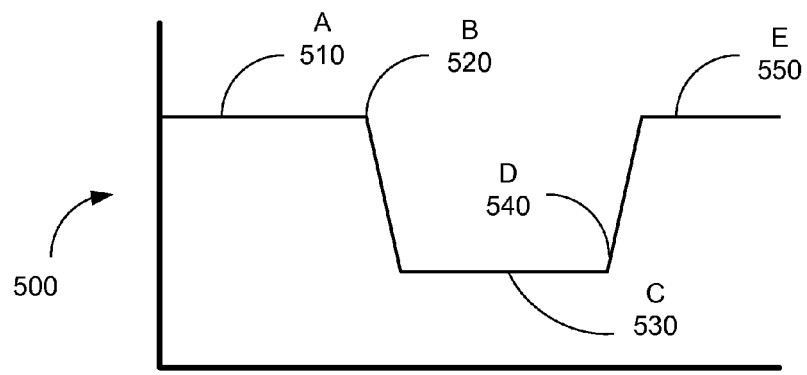
FIG. 5A is a diagram illustrating the typical effect of water on a mutual capacitive sense array, according to an embodiment of the invention.

FIG. 5A is a diagram 500 illustrating the typical effect of water on a mutual capacitive sense array, according to an embodiment of the invention. The diagram 500 depicts the capacitance measured on a mutual capacitive sense array, such as that shown in sense array 200, over changing environmental conditions.

At point A510, the sense array 200 is in its normal operation state with no touches, water, or other capacitance inducing events. At point B520, a water droplet is introduced on the sense array 200. Water induces an increased measured capacitance between electrodes on a mutual capacitive sense array. As a result, the sense array 200 experiences an increased measured capacitance in the presence of the water droplet, point C530. It should be noted that the measurements shown in FIGS. 5A-8 with respect to the measured capacitances are inverted to more easily describe the operation of the present invention. The quantitative amount of increased mutual capacitance depends upon the amount of water on the mutual capacitive sense array 200. At point D540, the water droplet is removed and the mutual capacitance sense array 200 returns to a normal "dry" state operational state, point E 550.

Figure 5B:
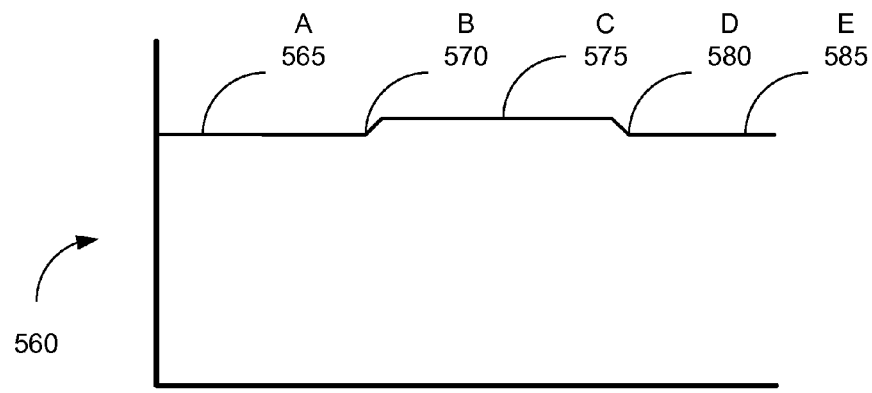
FIG. 5B is a diagram illustrating the typical effect of water on a self-capacitive sense array, according to an embodiment of the invention.

FIG. 5B is a diagram 560 illustrating the typical effect of water on a self-capacitance sense array, according to an embodiment of the invention. The diagram 560 depicts the capacitance measures on a self-capacitance sense array, such as that shown in sense array 400, over changing environmental conditions.

At point A565, the sense array 400 is in its normal operational state with no touches, water, or other capacitance inducing events. At point B570, a water droplet is introduced on the sense array 400. In contrast to FIG. 5A, water has relatively little effect on measured capacitance in self-capacitance sense arrays. To illustrate this property, the self capacitance of the TX and RX electrodes 350, 355 of FIG. 3 are represented by capacitors $C_P$ 330 and $C_P$ 335, respectively. As shown, the introduction of water on the sense array does not create an alternative conduction path between the upper conductive plates (UCP 340, 345) and lower conductive plates (LCP 360, 365) nor does it increase the capacitance between the upper and lower conductive plates. As a result, adding water on a self-capacitance sense arrays may have some, but no significant effect on the measured capacitance. At point C575, the measured self-capacitance slightly increases due to the water droplet. This may vary depending on the existence of shielding on the sense array 400, as further addressed below. At point D580, the self-capacitive sense array 400 returns to a normal "dry" operational state after the water droplet is removed, point E 585.

In alternative embodiments, the sense array 400 may have shielding. In standard driven shields, inactive electrodes (electrodes not currently being measured) are driven with the same waveform as the active electrodes by the driven shield, which may significantly reduce the effect of water on the sensor array. In grounded shielding, inactive electrodes are grounded by a grounded shield. In one embodiment, grounded and driven shields are used in conjunction with the self-capacitive scan and would be appreciated by those of ordinary skill in the art with the benefit of this disclosure.

Figure 6:
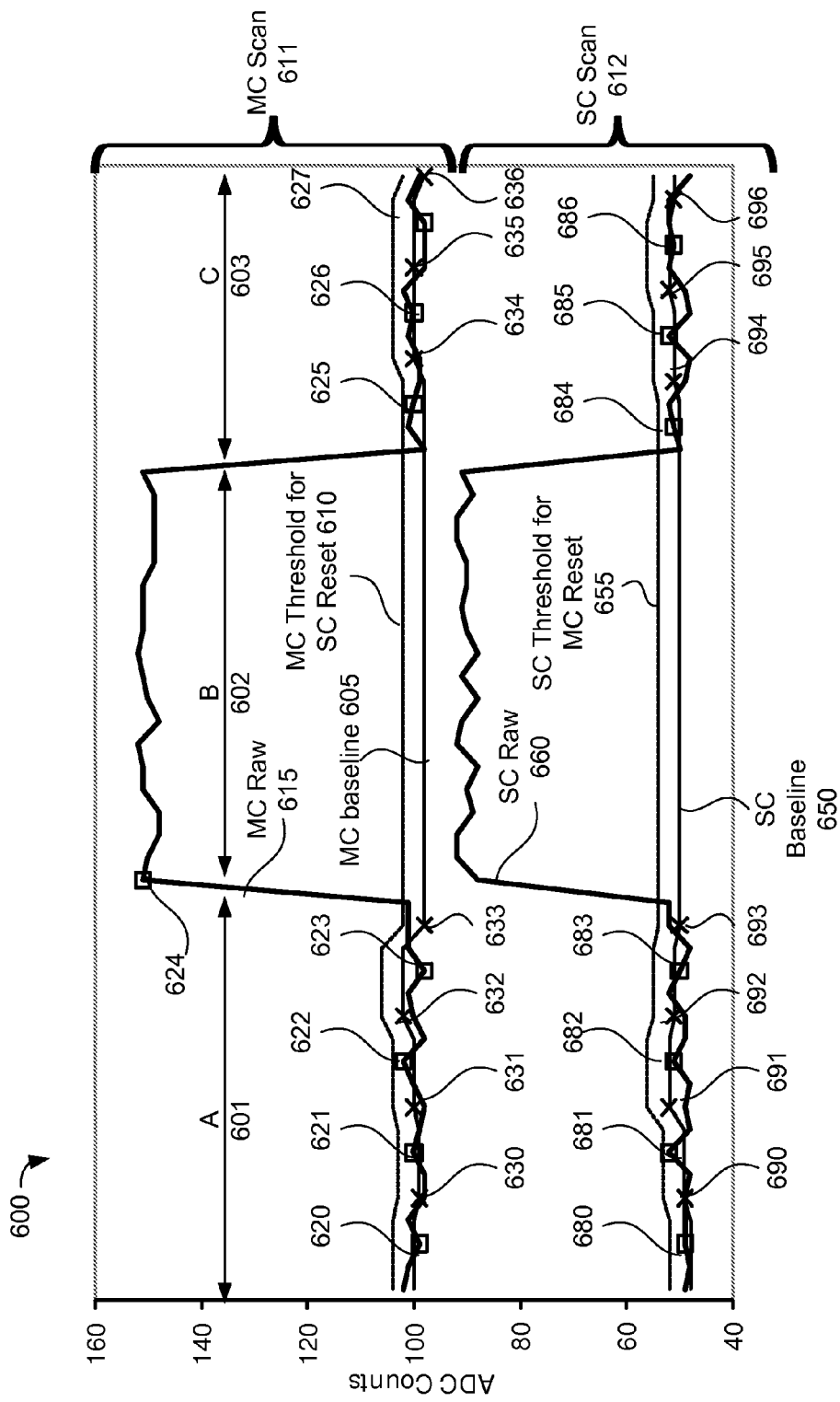
FIG. 6 is a diagram illustrating the electrical characteristics of a touch on a waterproof scanning array, according to an embodiment of the present invention.

FIG. 6 is a diagram 600 illustrating the electrical characteristics of a touch on a waterproof scanning array, according to an embodiment of the present invention. The waterproof scanning array (not shown) alternately performs a mutual capacitance all-points addressable scan ("MC scan 611") and a self-capacitance single electrode scan ("SC scan 612"). In one embodiment, the MC scan 611 and SC scan 612 have complimentary electrical properties when exposed to water as well as temperature (discussed below), and both exhibit a significant increase in capacitance with a touch. If one scan method detects a signal indicating a touch, but the other does not, no touch is reported. This prevents false touches during the time before the baseline is reset, as addressed below. If both scans detect a touch, a touch is reported. In an embodiment, the touch is a finger, stylus, or similar device. In one embodiment, the capacitance sensor 101 performs the functions and calculations executed for the waterproof scanning array.

MC scan 611 and SC scan 612 perform in alternate succession, maintaining a separate raw count and baseline for each. The raw count, or analog-to-digital ("ADC") count, is a digital value representative of the capacitance measured during a self-capacitance scan. The ADC count is an inverted digital representation of the capacitance measured during a mutual capacitance scan. The mutual capacitance ("MC") baseline 605 and the self-capacitance ("SC") baseline 650 represent the reference count value that the waterproof scanning array uses to determine whether a touch is detected. The MC threshold for SC reset ("MC threshold") 610 is the mutual capacitance upper boundary used to determine whether to update the SC baseline 650. The SC threshold for MC reset ("SC threshold") 655 is the self-capacitance upper boundary used to determine whether to update the MC baseline 605. MC raw count 615 and SC raw count 660 represent the measured ADC counts in the MC and SC scans, respectively. It should be noted that FIG. 6 depicts the MC baseline 605 and SC baseline 650 at ADC counts of approximately 100 and 50, respectively, for purposes of illustration and not necessarily to describe a preferred embodiment. In one embodiment, the ADC count is approximately 100 for both MC/SC scans 611, 612, when no touch object is present. In another embodiment, the ADC count for the touch threshold is approximately 20 above the MC and SC baselines 605, 650. In yet another embodiment, the ADC count for the MC and SC reset thresholds 610, 655 are approximately 3 above the MC and SC baselines 605, 650. FIG. 6 further illustrates a first no-touch period A601, a normal touch period B602, and a second no-touch period C603.

The MC/SC baselines 605, 650 are reset continuously, provided that adjacent sense elements scanned with the complimentary method do not detect a signal above their respective threshold value. For example, the SC scan 612 continuously updates the SC baseline 650, provided that the MC raw count 615 does not traverse the MC threshold for SC reset. In one embodiment, continuous reset does not mean every clock cycle. For example, the conditions that allow reset must be present for a predetermined number of cycles before the raw data is captured, and the conditions must remain true for an additional predetermined number of cycles before the captured raw data gets applied as the new baseline. This prevents resetting the baseline to an artificially high value if, for example, the baseline is set near the time that a contacting object is approaching or being lifted from the sense array, or if environmental conditions abruptly change. The MC scan 611 includes MC capture points 620-627 and MC reset points 630-636. The SC scan 612 includes SC capture points 680-686 and SC reset points 690-696. At each capture point, the sense algorithm compares raw count signals to the baseline and complimentary thresholds. In one embodiment, the baselines update approximately every 500 ms to keep up with environmental changes in temperature and humidity. The MC and SC reset points are points in time where the baseline resets to the prior capture point measurement.

During the first no-touch period A601, the capacitance sensor 101 measures the MC raw count 615 at MC capture point 620. In the complimentary SC scan, the SC raw count 660 is below SC threshold 655. As such, at MC reset point 630, the MC baseline 605 updates to the MC raw count 615 in MC capture point 620. Next, the capacitance sensor 101 measures the MC raw count 615 at MC capture point 621. In the complimentary SC scan, the SC raw count 660 is below SC threshold 655. As such, at MC reset point 631, the MC baseline 605 updates to the MC raw count 615 at MC capture point 621. The MC baseline 605 resets in similar fashion at reset points 632 and 633 for the entire span of the first no-touch period A601.

During normal touch period B602, a contacting object touches the waterproof scanning array. At MC capture point 624, the complimentary SC raw count 660 value is above the SC threshold value 655 and the MC baseline 605 is constant and remains that way during the span of the normal touch period B602.

The second no-touch period C603 begins after the contacting object is removed from the waterproof scanning array. The capacitance sensor 101 measures the MC raw count 615 at MC capture point 625. In the complimentary SC scan, the SC raw count 660 is below the SC threshold 655. As such, at MC reset point 630, the MC baseline 605 updates to the MC raw 615 count value in MC capture point 620. The MC baseline 605 resets in similar fashion at MC reset points 635 and 636 for the second no-touch period C603. In summary, at each MC reset point, the MC baseline 605 will continue to match the value of the MC raw 615 count at the previous capture point unless the complimentary SC threshold 655 count traverses by the SC raw signal. At that point, the MC baseline 605 will remain constant until the SC raw count 660 falls below the SC threshold 655.

The SC scan 612 is scanned alternately with the MC scan 611 and works in a similar fashion. For example, at each SC reset point during A601 and C603, the SC baseline 650 consistently updates to the previous SC capture point while the MC raw 615 count is below the MC threshold 610 count. Similarly, the SC baseline 650 remains constant during B602 because the complimentary MC raw count 615 traverses the MC threshold 610.

FIG. 6 shows data for only one mutual capacitive all-points addressable sense element and self-capacitive sense element to simplify the explanation of the operation. In one embodiment, the baseline update of the SC baseline 650 can be stopped by a signal from any mutual capacitive sense element on the same Rx line or adjacent Rx line. Similarly, the MC baseline 605 update can be prevented by a signal on the self-capacitive sense element shown or on either adjacent sense element in the sense array.

The waterproof scanning array of FIG. 6 also adapts to temperature change, according to an embodiment of the present invention. The SC and MC baselines 605, 650 continuously update to account for fluctuations in the MC and SC raw counts 615, 660. Mutual capacitance scanning has a negative temperature co-efficient, meaning the MC raw count 615 decreases as the ambient temperature increases. Self-capacitance scanning has a positive temperature co-efficient, meaning the SC raw count 660 increases as the ambient temperature increases.

Figure 7:
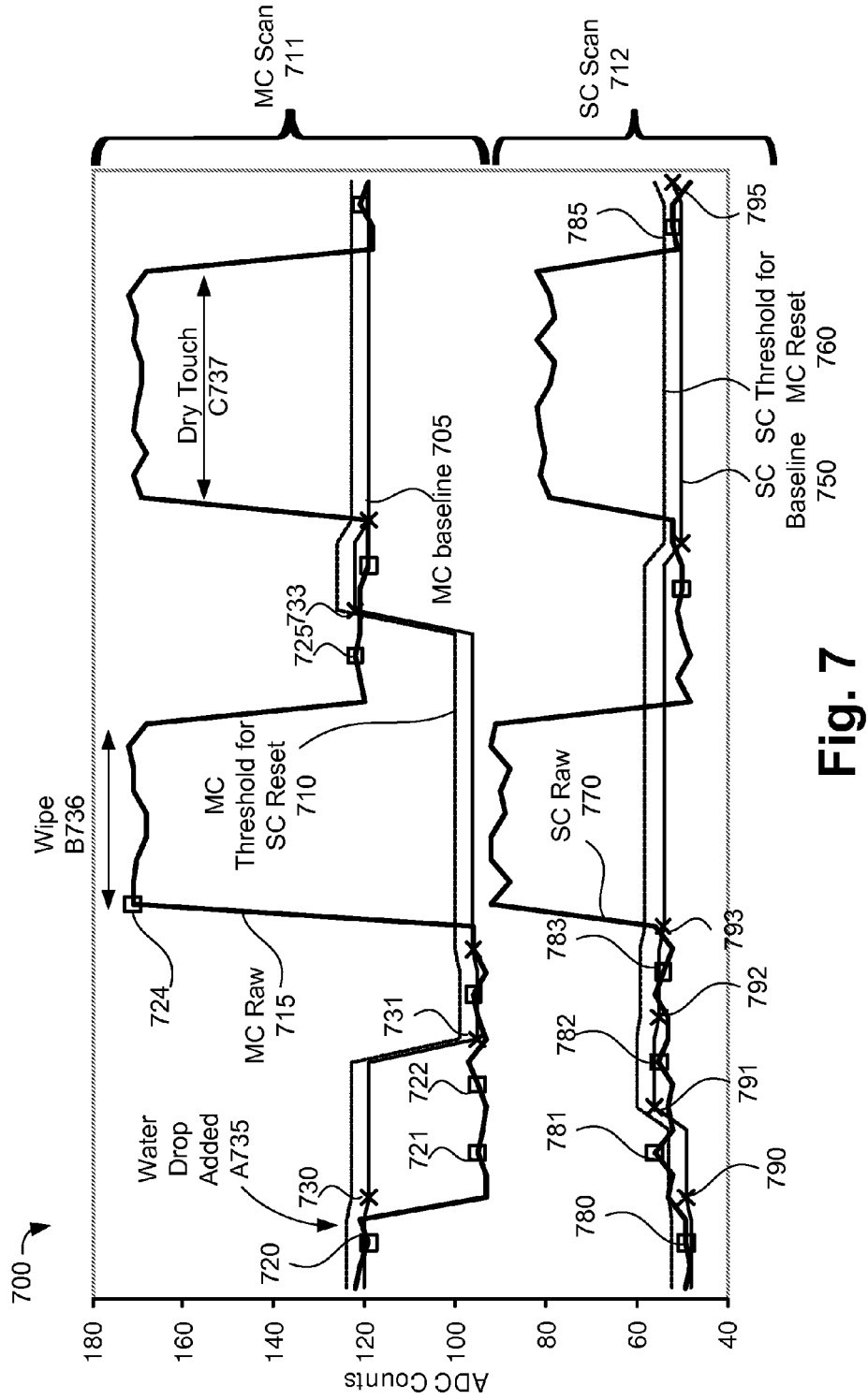
FIG. 7 is a diagram illustrating the effect of a water drop and touch on a waterproof scanning array, according to an embodiment of the present invention.

FIG. 7 is a diagram 700 illustrating the electrical characteristics of a touch on a waterproof scanning array, according to an embodiment of the present invention. The waterproof scanning array (not shown) alternately performs an MC scan 711 and SC scan 712. In an embodiment, the touch is a finger, stylus, or similar device. In one embodiment, the capacitance sensor 101 performs the functions and calculations executed on the functions and calculations executed for the waterproof scanning array.

Both scan methods 711, 712 perform in alternate succession, maintaining a separate raw count and baseline for each. MC scan 711 includes MC baseline 705, MC threshold for SC reset ("MC threshold") 710, MC raw count 715, MC capture points 720-727, and MC reset points 730-734. SC scan 712 includes SC baseline 750, SC threshold for MC reset ("SC threshold") 760, SC raw count 770, SC capture points 780-785, and SC reset points 790-795. FIG. 7 further includes A735 (water drop added), B736 (Wipe with finger), and C737 (Dry touch). It should be noted that FIG. 7 depicts the MC baseline 705 and SC baseline 750 at ADC counts of approximately 100 and 50, respectively, for purposes of illustration and not necessarily to describe a preferred embodiment. In one embodiment, the ADC count is approximately 100 for both MC/SC scans 611, 612, when no touch object is present. In an embodiment, the ADC count for the touch threshold is approximately 20 above the MC and SC baselines 705, 750. In another embodiment, the ADC count for the MC and SC reset thresholds 710, 760 are approximately 3 above the MC and SC baselines 705, 750.

In operation, the capacitance sensor 101 measures the MC raw count 715 at MC capture point 620. In the complimentary SC scan, the SC raw count 770 is below SC threshold 655. As such, at MC reset point 730, the MC baseline 705 updates to the MC raw count 615 in capture point 720.

A water drop is added at point A735, between the MC capture point 720 and MC reset point 730. Water causes the MC raw count 715 in a mutual capacitive sense array to drop due to the increased measured capacitance between electrodes, as described above in conjunction with FIG. 5A. The MC reset point 730 does not reflect the reduced MC raw count 715 because the reset point 730 refers back to the baseline value of the previous capture point 720 and adjusts the MC baseline 705 accordingly.

The MC baseline 705 is not reset to the MC raw 715 count in response to MC capture point 721 because the complimentary SC scan 712 crosses the MC threshold 760. As such, the MC baseline 705 remains constant. In contrast, the MC baseline 705 is reset to the previous MC capture point 722 at MC reset point 731 because the complimentary SC raw 770 count does not traverse MC threshold in SC scan 712. Thus, the MC baseline 705 adjusts to compensate for the reduced MC raw 715 count due to the water droplet.

The water droplet is wiped at B736. In one embodiment, the wipe both dries the water droplet off of the sense array and constitutes a touch by a finger 310. The MC baseline 705 is not reset in response to MC capture point 724 because the complimentary SC scan 712 crosses the MC threshold 760. The MC baseline 705 remains constant until MC reset point 733. At the end of the wipe B736, the sense array is dry and the MC raw count 715 returns to a normal non-touch, dry raw count value. In some embodiments, there may be a short delay between the actual reduction of MC raw count 715 and the MC baseline 705 correction, as shown at MC reset point 733. In another embodiment, the delay is improved with an increased number MC capture and MC reset points. During dry touch C737, the capacitance sensor 101 reads a touch with a fixed MC baseline 705 similar to FIG. 6.

For SC scan 712, the SC baseline 750 slightly increases due to the water drop at A735, but returns to normal levels after the wipe B736. The SC scan 712 and the capacitance sensor 101 execute similarly as that which is described in the SC scan 612 of FIG. 6. A touch is detected when both the MC and SC thresholds 710, 760 are traversed by raw counts 715, 770. This occurs during the wipe B736 and dry touch C737.

Figure 8:
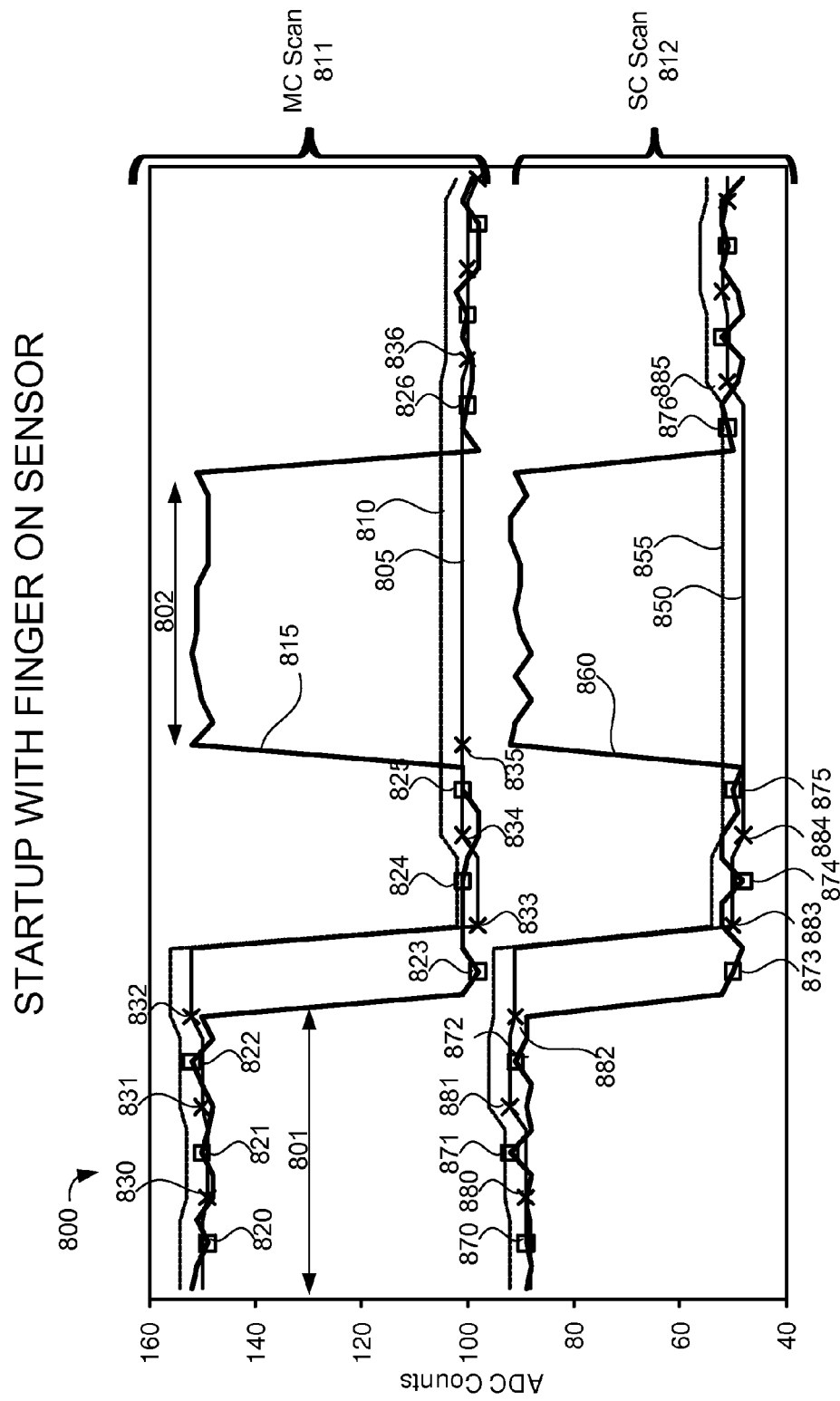
FIG. 8 is a diagram illustrating the effect of a finger present at startup on a waterproof scanning array, according to an embodiment of the present invention.

FIG. 8 is a diagram 800 illustrating the electrical characteristics of a finger present at startup on a waterproof scanning array, according to an embodiment of the present invention. The waterproof scanning array alternately performs an MC scan 811 and SC scan 812. In an embodiment, the touch is a finger, stylus, or similar device. In one embodiment, the capacitance sensor 101 performs the functions and calculations executed on the functions and calculations executed for the waterproof scanning array.

Both scan methods 811, 812 perform in alternate succession, maintaining a separate raw count and baseline for each. MC scan 811 includes MC baseline 805, MC threshold for SC reset ("MC threshold") 810, MC raw count 815, MC capture points 820-826, and MC reset points 830-836. SC scan 812 includes SC baseline 850, SC threshold for MC reset ("SC threshold") 855, SC raw count 860, SC capture points 870-876, and SC reset points 880-885. FIG. 8 further includes A801 (finger at startup) and B802 (dry touch). It should be noted that FIG. 8 depicts the MC baseline 805 and SC baseline 850 at ADC counts of approximately 100 and 50, respectively, for purposes of illustration and not necessarily to describe a preferred embodiment. In one embodiment, the ADC count is approximately 100 for both MC/SC scans 811, 812, when no touch object is present. In an embodiment, the ADC count for the touch threshold is approximately 20 above the MC and SC baselines 805, 850. In another embodiment, the ADC count for the MC and SC reset thresholds 810, 855 are approximately 3 above the MC and SC baselines 805, 850. In another embodiment, a touch is performed by a stylus, finger, or other touching object known to those skilled in the art.

The MC raw count 815 at MC capture point 820 is elevated due to a touch being present on the water rejection sense array during startup A801. After the touch is removed, the MC raw count 815 drops to nominal no-touch MC raw count levels and is read at MC capture point 823. In the complimentary SC scan 812, the SC raw 860 count is below the SC threshold 855. The MC reset point 833 adjusts the MC baseline 805 to match the MC raw count 815 detected at MC capture point 823. The MC and SC scans 811, 812, execute touch detection for dry touch period B802 similar to that which is described for B602 of FIG. 6.

Figure 9:
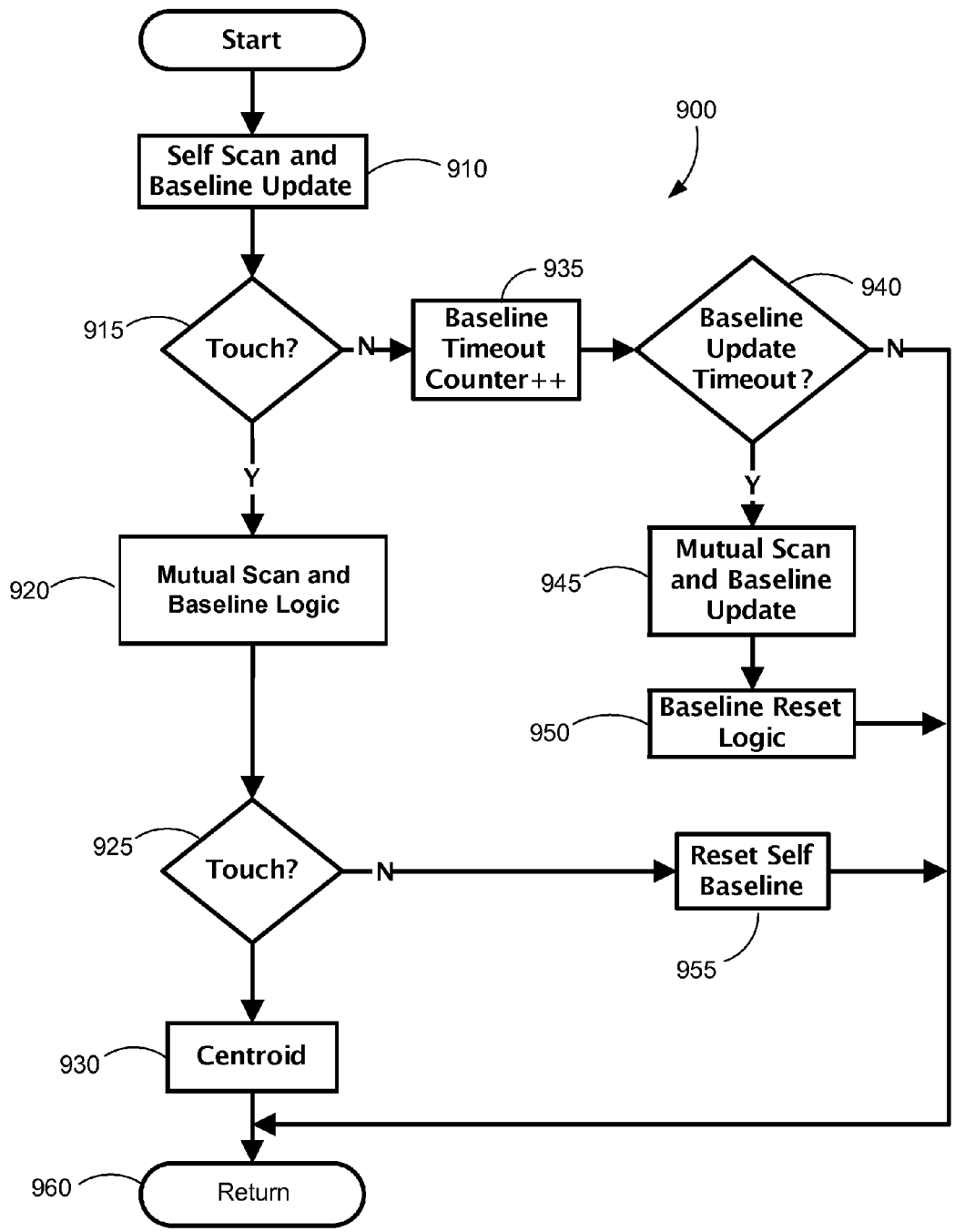
FIG. 9 is a flow chart of one embodiment of a method for waterproof scanning on a sense array with reduced power consumption, according to an embodiment of the present invention.

FIG. 9 is a flow chart of an embodiment of a method 900 for waterproof scanning on a sense array (not shown) with reduced power consumption using both a mutual capacitance scan ("mutual scan") and self-capacitance scan ("self-scan"). In one embodiment, method 900 will only execute self-scans until a touch is detected. The mutual scan is performed to both validate and find the precise location of the touching object. If the self-scan does not detect a touch, the mutual scan is skipped to conserve power, as further detailed below.

In one embodiment, the method 900 is an algorithm executed in firmware and begins by performing a self-scan and baseline update (block 910). In one embodiment, the purpose of the self-scan is to reduce the average power of the sense array and provide data for the water rejection algorithm. As discussed above in conjunction with FIG. 5B, in contrast to mutual scans, water has little effect on the measured self-scan capacitance of the sense array. Furthermore, self-scan data helps the water rejection algorithm by keeping a relevant mutual baseline and validating mutual touches, as described above in conjunction with FIG. 7. The self-scan measures mutual Rx electrodes, such as Rx electrode 223 of FIG. 2, and determines which of the electrodes has a touch present. In one embodiment, self scanning is limited to the Rx electrodes because they are already configured for optimal channel usage. Furthermore, only one axis of self-data is required to achieve the functional requirement of determining whether a touch exists, not where the touch is located. In one embodiment, the self-scan uses a driven shield, where inactive electrode are driven with the same waveform as the active electrodes, which significantly helps in reducing any raw count change due to water.

If the self-scan detects a possible touch (block 915), then the water rejection algorithm executes a mutual capacitance scan to validate the touch (block 920). A touch occurs when both the self-scan and mutual scan report a touch. In addition to validating the touch, the mutual scan determines the precise location of the touching object. If both scans report a valid touch (block 925), then a centroid calculation is performed (process block 930), and the process returns to the beginning (block 960). The centroid algorithm determines the precise location of the touching object. If the mutual scan does not report a valid touch, the self-scan baseline resets (block 955).

If a touch is not detected by the self-scan (block 915), then the baseline timeout counter is incremented (block 935). The timeout counter ensures that if there is no touch detected within the baseline update timeout period (block 940), a mutual capacitive scan is performed (block 945) and the baselines are reset (block 950) according to the logic described in FIGS. 6-8. This results in a mutual capacitive scan occurring less frequently which saves power, but ensures that there is not too much time between mutual capacitive scans to maintain accurate baselines during slow temperature changes or other environmental conditions. After the baseline logic is reset (block 950), the process returns to the beginning (block 960). If the baseline update timeout period has not ended, the process returns to the beginning (block 960).

The particular features, structures or characteristics described herein may be combined as suitable in one or more embodiments of the invention. In addition, while the invention has been described in terms of several embodiments, those skilled in the art will recognize that the invention is not limited to the embodiments described. The embodiments of the invention can be practiced with modification and alteration within the scope of the appended claims. The specification and the drawings are thus to be regarded as illustrative instead of limiting on the invention.

What is claimed is:

1. A capacitance sensing device comprising:
a first plurality of capacitance sensing electrodes disposed along a first axis;
a second plurality of capacitance sensing electrodes disposed along a second axis, the second axis substantially perpendicular to the first axis; and
a controller configured to:
measure a self capacitance of either: at least one of the first plurality of capacitance sensing electrodes or at least one of the second plurality of capacitance sensing electrodes and update a mutual capacitance baseline based on the measured self capacitance in a first mode,
measure a mutual capacitance between at least one of the first plurality of capacitance sensing electrodes and at least one of the second plurality of capacitance sensing electrodes and update a self capacitance baseline based on the measured mutual capacitance in a second mode,
identify a touch on the capacitance sensing device if the measured self capacitance is above a first self capacitance threshold and if the measured mutual capacitance is above a first mutual capacitance threshold so as to prevent reporting of false touches before one or more of the baselines is updated, and calculate a position of the touch on the capacitance sensing device based on one or more of the measured self capacitance and the measured mutual capacitance.

2. The capacitance sensing device of claim 1, wherein the first plurality of capacitance sensing electrodes are configured as transmit electrodes and the second plurality of capacitance sensing electrodes are configured as receive electrodes in the second mode.

3. The capacitance sensing device of claim 1, wherein the controller alternates between the first mode and the second mode to measure self capacitance and mutual capacitance.

4. The capacitance sensing device of claim 1, wherein the controller is configured to measure the mutual capacitance between at least one of the first plurality of capacitance sensing electrodes and at least one of the second plurality of capacitance sensing electrodes only if the measured self capacitance is above the first self capacitance threshold.

5. The capacitance sensing device of claim 1, wherein the controller is configured to calculate the position of the touch on the capacitance sensing device based on the measured mutual capacitance.

6. The capacitance sensing device of claim 1, wherein the controller comprises:
a first measurement circuit configured to measure self capacitance; and
a second measurement circuit configured to measure mutual capacitance.

7. The capacitance sensing device of claim 1, wherein the controller comprises a measurement circuit configured to measure self capacitance in the first mode and measure mutual capacitance in the second mode.

8. The capacitance sensing device of claim 1, wherein the controller is configured to drive either: a first inactive subset of the first plurality of capacitance sensing electrodes or a second inactive subset of the second plurality of capacitance sensing electrodes with a shield signal while measuring the self capacitance in the first mode so as to reduce measurement effects caused by water in proximity to a sensor array of the capacitance sensing device.

9. A method comprising:
measuring a self capacitance of at least one of a first plurality of capacitance sensing electrodes and updating a mutual capacitance baseline based on the measured self capacitance;
measuring a mutual capacitance between at least one of the first plurality of capacitance sensing electrodes and at least one of a second plurality of capacitance sensing electrodes, wherein the second plurality of capacitance sensing electrodes is disposed substantially perpendicular to the first plurality of capacitance sensing electrodes;
recognizing a touch on a surface above the first and second pluralities of capacitance sensing electrodes if the measured self capacitance is above a first threshold and the measured mutual capacitance is above a second threshold so as to prevent reporting of false touches before the mutual capacitance baseline is updated;
calculating a first position of the touch on the surface based on the measured capacitances.

10. The method of claim 9, wherein the measuring a mutual capacitance occurs if the measured self capacitance is above a third threshold.

11. The method of claim 9, wherein a first calculated position is based on only the measured mutual capacitance.

12. The method of claim 9, further comprising:
measuring the self capacitance of at least one of the second plurality of capacitance sensing electrodes; and
calculating a second position based on the measured self capacitance on the first and second pluralities of electrodes.

13. The method of claim 9, wherein the self capacitance measurement is performed by a first measurement circuit and the mutual capacitance measurement is performed by a second measurement circuit.

14. The method of claim 9, wherein the self capacitance measurement and the mutual capacitance measurement are performed by a single measurement circuit operating in a first mode self capacitance measurement and in a second mode for mutual capacitance measurement.

15. The method of claim 9, wherein the measuring the self capacitance of the at least one of a first plurality of capacitance sensing electrodes comprises:
driving a first inactive electrode of the first plurality of capacitance sensing electrodes with a shield signal; and
measuring the self capacitance of a second electrode of the first plurality of capacitance sensing electrodes, the second electrode being substantially adjacent to the first electrode, so as to reduce measurement effects caused by water in proximity to the first electrode.

16. A touch screen controller configured to:
measure a self capacitance of at least one of a first plurality of capacitance sensing electrodes in a first mode and update a mutual capacitance baseline based on the measured self capacitance;
measure a mutual capacitance between at least one of the first plurality of capacitance sensing electrodes and at least one of a second plurality of capacitance sensing electrodes in a second mode;
identify a touch on the capacitance sensing device if the measured self capacitance is above a first self capacitance threshold and if the measured mutual capacitance is above a first mutual capacitance threshold so as to prevent reporting of false touches before the mutual capacitance baseline is updated; and calculate a position of the touch on the first and second pluralities of a capacitance sensing electrodes.

17. The touch screen controller of claim 16, further configured to alternate between the first mode and the second mode to measure self capacitance and mutual capacitance.

18. The touch screen controller of claim 16, further configured to measure the mutual capacitance between at least one of the first plurality of capacitance sensing electrodes and at least one of the second plurality of capacitance sensing electrodes only if the measured self capacitance is above the first self capacitance threshold.

19. The touch screen controller of claim 16, comprising:
a first measurement circuit configured to measure self capacitance; and
a second measurement circuit configured to measure mutual capacitance.

20. The touch screen controller of claim 16, further configured to drive either: a first inactive subset of the first plurality of capacitance sensing electrodes or a second inactive the second plurality of capacitance sensing electrodes with a shield signal while measuring self capacitance in a first mode so as to reduce measurement effects caused by water in proximity to a sensor array associated with the touch screen controller.

* * * * *